United States Patent [19]

Sapienza et al.

[11] Patent Number: 4,460,710

[45] Date of Patent: Jul. 17, 1984

[54] CATALYTIC METHOD FOR SYNTHESIZING HYDROCARBONS

[75] Inventors: Richard S. Sapienza, Shoreham, N.Y.; Michael J. Sansone, Summit, N.J.; William A. R. Slegeir, Hampton Bays, N.Y.

[73] Assignee: The United States of America as represented by the United States Department of Energy, Washington, D.C.

[21] Appl. No.: 485,349

[22] Filed: Apr. 15, 1983

Related U.S. Application Data

[62] Division of Ser. No. 293,043, Aug. 14, 1981, Pat. No. 4,396,539.

[51] Int. Cl.$^3$ .............................................. C07C 1/04
[52] U.S. Cl. ................................................... 518/700
[58] Field of Search ................................. 518/700, 715

[56] References Cited

U.S. PATENT DOCUMENTS 3,988,334 10/1976 Finch et al. .

Primary Examiner—Howard T. Mars
Attorney, Agent, or Firm—Margaret C. Bogosian; Paul A. Gottlieb; Michael F. Esposito

[57] ABSTRACT

A method for synthesizing hydrocarbons from carbon monoxide and hydrogen by contacting said gases with a slurry of a catalyst composed of palladium or platinum and cobalt supported on a solid phase is disclosed. The catalyst is prepared by heating a heterogeneous component of the palladium or platinum deposited on the solid support in a solution of cobalt carbonyl or precursors thereof. The catalyst exhibits excellent activity, stability in air, and produces highly desirable product fractions even with dilute gaseous reactants.

7 Claims, 9 Drawing Figures

"ALLOY" STRUCTURE

Fig. 4

LAYERED STRUCTURE

Fig. 5

PARAFFIN CARBON NUMBER
PROD. DIST.
INSTANT INVENTION

Fig. 6

PARAFFIN CARBON NUMBER
DIESEL FUEL

CATALYTIC METHOD FOR SYNTHESIZING HYDROCARBONS

BACKGROUND OF THE INVENTION

The U.S. Government has rights in this invention pursuant to Contract Number DE-AC02-76CH00016, between the U.S. Department of Energy and Associated Universities, Inc.

RELATED APPLICATIONS

This application is a divisional application of copending U.S. patent application Ser. No. 293,043, filed Aug. 14, 1981, now U.S. Pat. No. 4,396,539.

FIELD OF THE INVENTION

This invention relates to the synthesis of hydrocarbons by the reaction of carbon monoxide and hydrogen in the presence of a catalyst, commonly known as the Fischer-Tropsch synthesis. More particularly, this invention relates to novel catalysts for use in such process, methods for preparation of such catalysts, and methods for use of such catalysts.

DESCRIPTION OF THE PRIOR ART

The so-called Fischer-Tropsch synthesis wherein liquid aliphatic hydrocarbons, alcohols and minor amounts of aldehydes, fatty acids and ketones are produced by the hydrogenation of carbon monoxide has been known for about 60 years. Initially, alkalized iron turnings were utilized as the catalytic material. Typical effective catalysts are supported cobalt-thoria or supported iron catalysts. The reaction temperature is about 250°–300° C. and pressures range from 1 atm. to about 20 atm. A large commercial plant using iron catalysts is in operation in South Africa. Additionally, various methods for conducting the specific contacting of the reactants with one another and the catalytic material have been utilized, e.g. fixed bed, fluidized bed, etc. A thorough discussion of the chemistry of this immensely important reaction is set forth in "The Fischer-Tropsch and Related Syntheses" by Henry H. Storch, Norma Golumbic, Robert B. Anderson, published by John Wiley & Sons, New York, 1951.

Numerous attempts have been made to refine this synthesis in terms of improved effectiveness of the catalyst, product yield, improved production of more desirable product fractions, control of the product distribution, etc. Additionally, efforts have been made to achieve more stable catalysts. As a general rule, the materials which have been known to be effective as Fischer-Tropsch catalysts are extremely sensitive to air and moisture and consequently, must be used either shortly after preparation or prepared in situ.

In more recent years, the catalysts used for such reactions were composed of cobalt, sometimes in conjunction with nickel on a support, such as a clay. These catalysts have generally been characterized by instability and low activity. Additionally, such catalysts require the use of either a fixed or fluidized bed type system. Such contacting methods often produce severe heat transfer problems which place an additional burden upon the process as well as affect the uniformity of the products obtained.

SUMMARY OF THE INVENTION

We have discovered a novel catalytic material which can be used for the synthesis of hydrocarbons from carbon monoxide and hydrogen. This catalytic material is unique in both its physiochemical constitution as well as the properties which it exhibits. Thus, the catalytic composition of the present invention exhibits superior activity as compared to conventional Fischer-Tropsch type catalysts. In addition, such activity can be obtained in dilute slurry form which substantially improves the heat transfer factors involved in the Fischer-Tropsch synthesis. Furthermore, the catalytic composition of the present invention exhibits superior stability and can be stored for long periods of time in either a dry or slurry form. Finally, the catalytic composition of the present invention produces a very desirable product composed of a fraction of linear hydrocarbons ranging from $C_1$ to $C_{40}$ with a low degree of branching.

The catalyst composition of the present invention is easily prepared by a new process which also comprises a part of the present invention. This process allows the composition to be prepared and separated for use at a later time.

The method and use of the present invention is also unique as compared with conventional Fischer-Tropsch catalysts. Of great importance is the fact that this catalyst can be used in dilute slurry form and with dilute concentrations of gaseous reactants to obtain high yields of desirable product fractions. This avoids the heat transfer problems commonly encountered with alternative contacting systems.

More particularly, the catalyst composition of the present invention is composed of palladium or platinum and cobalt supported on a solid phase. The solid phase material, commonly referred to as a support or carrier, may be chosen from any appropriate material such as: talc; dolomite; limestone; clay; activated carbon; zeolite; pumice; the oxides, hydroxides or carbonates of aluminum, silicon, zinc, chromium, magnesium, calcium, titanium, or zirconium; alumina; silica gel; kieselguhr; barium sulfate; or any inert material. This catalyst produces improved yields significantly greater than conventionally known systems. Additionally, the catalyst is able to operate effectively under wider ranges of pressure and temperature than the previously known catalysts and can also operate effectively under dilute feed gas conditions, that is in the presence of synthesis gas diluents or impurities such as nitrogen, so long as the ranges of carbon monoxide and hydrogen are within the ranges set forth below.

The catalyst of the present invention is prepared by first heating a heterogeneous component. As used herein, the term heterogeneous component means a component formed from two different materials, i.e, a metal and a support. Typically, the heterogeneous component would be palladium or platinum on a solid phase support. This heterogeneous component is heated in a homogeneous phase which is composed of a metal carbonyl or metal precursor compound. As used herein, the term metal precursor compound means a compound, which, on heating, forms the metal carbonyl in situ. This metal carbonyl or precursor is in a suitable solvent and the heating takes place in a gaseous stream of hydrogen and carbon monoxide. The heating time and temperature as well as the pressure of the hydrogen and carbon monoxide can be varied, but in any event, must be sufficient to form the catalyst. The completion of the catalyst preparation is indicated by a disappearance of the color of the metal carbonyl. Alternately, or simultaneously, the process can be monitored by infrared analysis to detect the metal carbonyl absorption. When this absorption no longer exists, the preparation of the catalyst is complete.

The catalyst of the present invention can be used to synthesize hydrocarbons from a mixture of hydrogen and carbon monoxide by contacting the gaseous mixture with a solvent and an effective amount of the catalyst in a slurry form.

DESCRIPTION OF THE PREFERRED EMBODIMENTS

More particularly, the catalyst of the present invention is formed from palladium or platinum on a solid phase having cobalt supported thereon wherein the amount of palladium or platinum is in the range from about 0.1 to 10 weight percent based on the total weight of the catalyst. The cobalt may be present in the range from about 10 to 70 weight percent based on the total weight of the catalyst.

A variety of supports may be used and these are well known in the art. Typically, such supports would include alumina, silica gel, kieselguhr and zinc oxide.

Figure 1:
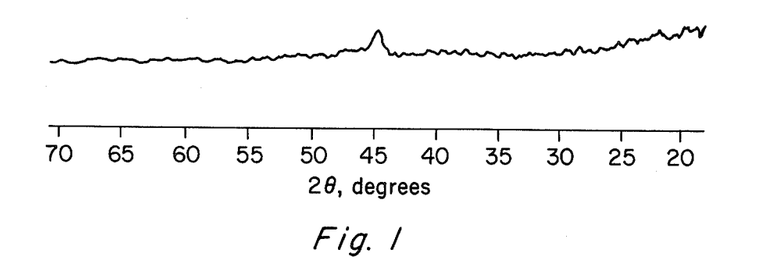
FIG. 1 is an X-ray diffraction pattern of a catalyst in accordance with the present invention.
Figure 2:
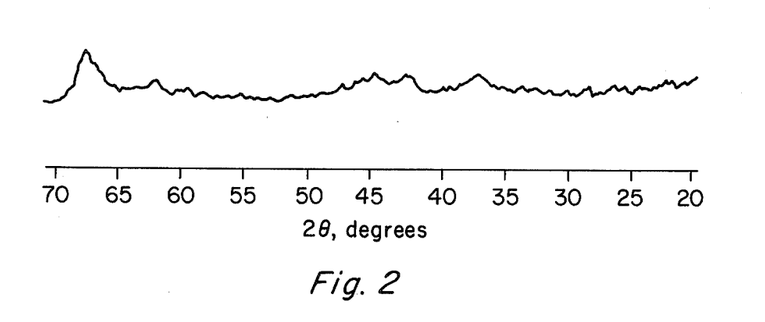
FIG. 2 is an X-ray diffraction pattern of a catalyst not in accordance with the present invention.

The catalytic composition of the present invention possesses a unique structure which can be characterized by the X-ray diffraction patterns of the catalytic composition. In particular, reference is made to FIGS. 1 and 2. FIG. 1 is an X-ray diffraction pattern of a catalyst in accordance with the present invention composed of cobalt and palladium on an aluminum oxide carrier. In contrast, FIG. 2 is an X-ray diffraction pattern of a cobalt/aluminum oxide catalyst prepared by standard precipitation techniques. It is clear that as a result of the unique structure of the present catalyst, the aluminum oxide peak between 65 and 70 does not appear. (In X-ray diffraction patterns of this type, $2\theta$ equals around 65–70, where $\theta$ equals the angle of refraction.) Thus, because of the actual physical structure of the present catalyst, the aluminum oxide pattern is comletely masked. In each case, however, it is clear that the cobalt peaks at about 45 come through.

Figure 3:
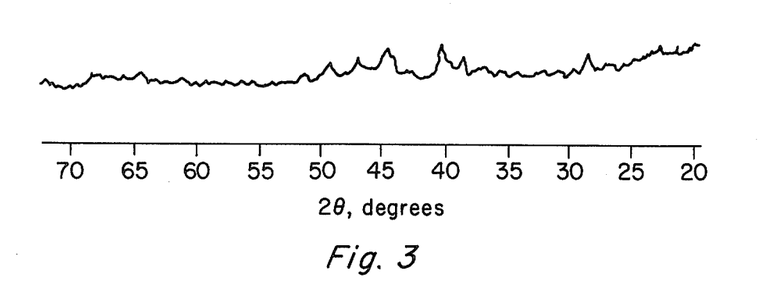
FIG. 3 is an X-ray diffraction pattern of a catalyst in accordance with the present invention.

A comparison of the X-ray diffraction patterns of the catalyst of FIG. 1 and a similar catalyst having a lower cobalt loading, (catalyst of FIG. 1 is 55% by weight cobalt while the catalyst in FIG. 3 is 28% by weight cobalt) is shown in FIG. 3. This comparison indicates that while the cobalt peaks still appear around 45, the aluminum oxide peak present in the standard catalyst between 65 and 70 still is not seen.

It is believed that the reason for this is that the structure of the present catalyst is one wherein the cobalt and palladium or platinum coats the support in a manner which completely shields the support from the X-ray analysis as compared to the prior art materials wherein the deposited metal was sufficiently diffused to allow the support to be reached by the X-ray beam. What is of particular interest, however, is the fact that even at relatively low cobalt loadings, the support is still not seen in the X-ray diffraction pattern. The coating of the support that takes place in the preparation of the catalysts of the present invention could theoretically occur in such a way as to produce structures as depicted in FIGS. 4 and 5.

Figures 4, 5, 6:
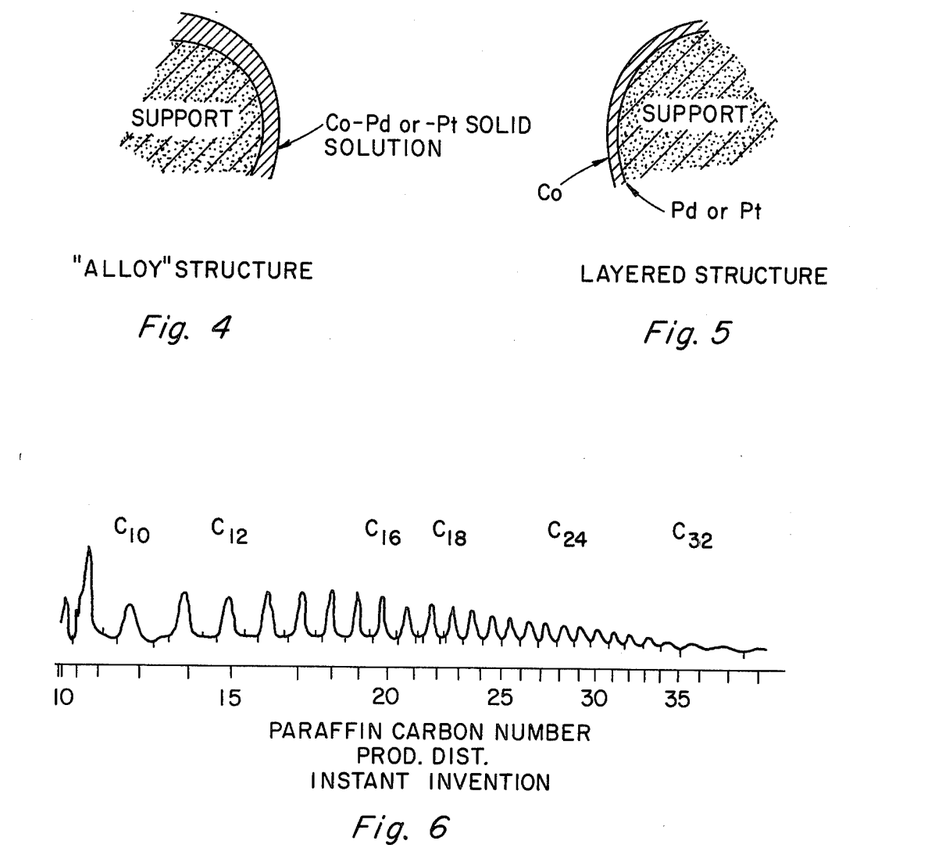
FIG. 4 is a cross-sectional diagram of a solid solution catalyst not in accordance with the present invention.
FIG. 5 is an "idealized" cross-sectional diagram of a catalyst particle of the present invention.
FIG. 6 is a gas chromatographic analysis of the product obtained with the process of the invention.

In particular, as shown in FIG. 4, the catalyst of the present invention may comprise particles of a catalytic support which are surrounded by an X-ray impermeable layer of a solid solution of platinum or palladium with cobalt. The same effect may be achieved by the structure shown in FIG. 5 wherein a first inner layer of platinum or palladium surrounds the support in a manner to be X-ray impermeable and a second layer of cobalt is superimposed thereon. However, as the palladium peaks are clearly visible in FIG. 3, but not in FIG. 1, reflecting the shielding effect of cobalt, FIG. 5 would appear to best represent the idealized structure of this catalyst.

The unique catalytic composition of the present invention is obtained by a novel process. The first step of the process involves the conventional deposition of palladium or platinum or mixtures thereof on to a solid phase.

Typically, this is accomplished by impregnation of the support with an aqueous solution of a salt of the particular metal. For example, such preparations are shown in U.S. Pat. No. 3,988,334, incorporated herein by reference. In the usual process, the support, such as alumina, silica, zirconia, silica-alumina, kieselguhr, and the like, in particulate form is immersed in an aqueous solution of a salt of the particular metal. After sufficient time for impregnation of the support, the mixture is dried at temperatures between 80°–200° C., usually in air, and ultimately calcined in air for a period from one half to one and one half hours at temperatures between 300°–600° C. Those skilled in the art will readily recognize that other methods are available, such as the known techniques of sputtering, other methods of precipitation, vapor deposition, electrical deposition and electrochemical deposition.

In accordance with a novel aspect of the present invention, the thus prepared platinum or palladium on the support is then immersed into a solution of cobalt carbonyl, or hydride cobalt carbonyl precursors thereof, in an appropriate solvent. The forms of the cobalt can be selected from either the metallic form, the complexed form, or the salt form. In the latter, the salt can be any inorganic salt or organic salt capable of being converted into an organic solvent soluble form under reaction conditions. Of course, it is understood, that any cobalt compound which might be known to inhibit the ultimate action of the catalyst is to be avoided.

One of the interesting characteristics of cobalt carbonyl is that solutions containing cobalt carbonyl generally have a dark color, usually brown. This is important in determining when the reaction of the cobalt carbonyl with the other components of the catalyst is complete.

The cobalt carbonyl or the precursor thereof and the support carrying the platinum or palladium are placed in an appropriate organic solvent which can be selected from a wide variety of known materials. Suitable solvents include, for example, saturated hydrocarbons, such as n-hexane, and cetane, slack wax, aliphatic alcohols, such as butanol and isooctanol, aldehydes, and the like or the alcohol or ether by-products of the oxo process, such as, isooctanol, isobutanol, and ethers, either taken alone or mixed. Those skilled in the art may readily recognize that the use of less inert solvents, such as olefins, is possible, resulting in their incorporation into the product. Particulary preferred solvents are cyclohexane, xylene, decalin, and tetrahydrofuran.

The mixture of the support carrying the platinum or palladium with the cobalt carbonyl or its precursor in the solvent is placed under an inert atmosphere and then subjected to pressure using "syngas", i.e., carbon monoxide and hydrogen. The process can be carried out under either a static pressure or in a continuous manner. Typically, the partial pressure of syngas utilized is between about 3 to 3,000 psi and the mixture is agitated at a temperature from about 100° to 350° C. If the carbon monoxide pressure is too high, the cobalt tends to go back into the solution.

In the static type situation, the entire mixture is placed into a pressure bomb which is agitated, as by shaking. Alternately, an internal mixing or stirring device can be utilized.

In any event, the reaction is continued until the color of the cobalt carbonyl disappears from the solution which can be determined either visually or by infrared spectroscopy by measuring the disappearance of the characteristic metal carbonyl absorptions in the range of 2100–1600 cm$^{-1}$.

Insofar as the gaseous composition utilized in the preparation process is concerned, one can use a ratio of hydrogen to carbon monoxide in the range from about 11:1 to 1:4, and preferably in the range from 2:1 to 1:1. Hydrogen gas alone may be used in place of syngas for the preparation of the catalyst.

After the reaction has been completed, the catalyst, still in particulate form, can be separated from the solvent by standard separation techniques, e.g., magnetic techniques, precipitation, filtration, centrifugation, and the like. The catalyst can then be stored either in the moist form or after having been dried at relatively low temperatures, i.e., under 300° C., and preferably under 120° C., for extended periods of time without any additional precautions being taken. Thus, the catalyst of the present invention does not lose its activity as a result of contact with air, even after long periods of time on the shelf.

The catalyst thus prepared exhibits the X-ray diffraction characteristics as exhibited in FIG. 1. Of particular interest, however, is a comparison of the X-ray diffraction patterns of a catalyst prepared in accordance with the present invention as shown in FIG. 1 and that wherein cobalt carbonyl is deposited solely on an aluminum oxide support without having any palladium or platinum deposited thereon. The X-ray diffraction of this latter catalyst is shown in FIG. 2. As can be seen, the single sharp peak found in FIG. 1 at around 45 shows that the cobalt in the catalyst of the present invention has a highly structured crystalline form which is believed to be face centered cubic in contrast to the multiple diffuse peaks of FIG. 2, which shows a mixture of cobalt crystalline forms.

The method of use of the present catalyst is also novel and advantageous. Not only can the present catalyst be used in the conventional so-called fixed bed or fluidized bed reactions, but it can also be used in a slurry type reactor. The conventional contacting techniques, i.e, fixed or fluidized bed, suffer from the disadvantages that localized hot spots can develop due to poor heat transfer and the relatively high concentration of catalyst. This can affect both the efficiency of the process and the product distribution and uniformity. When the catalyst of the present invention is used in the slurry type reactor, the catalyst can be used in relatively dilute form and can also be used efficiently with dilute gaseous mixtures.

In contrast to the conventional contacting techniques, with a relatively dilute slurry of the catalyst in a solvent, the heat transfer within the system is more efficient than with the other techniques and these problems can be avoided. Additionally, the synthesis reaction with the present catalyst can be carried out at a wide variety of temperatures and pressures.

In particular, the catalyst of the present invention can be utilized in slurry form in the conventional solvents used for such reactions. The slurry concentration can generally be in the range from about 0.3 to 50 percent by volume. This can, of course, be varied depending on the desired results. Slurry concentrations of from about 1 to 300 g/l are preferred.

Suitable temperatures for carrying out a synthesis reaction with the present invention range from about 30° to 400° C., and, preferably, are in the range from about 130° to 250° C.

As noted, relatively dilute concentrations of gaseous reactants, i.e. hydrogen and carbon monoxide, can be used. Conditions for use are essentially the same as conditions for preparation; however, as the syngas pressure increases, the product distribution begins to favor oxygenates such as alcohols, ketones, and the like. Overall partial pressures of hydrogen in the total mixture from about 2 to 2500 psi can be employed, with pressures from about 100 to 1000 psi being preferred; and carbon monoxide pressures from about 1 to 2000 psi, and preferably, from about 60 to 600 psi can be used.

Figure 7:
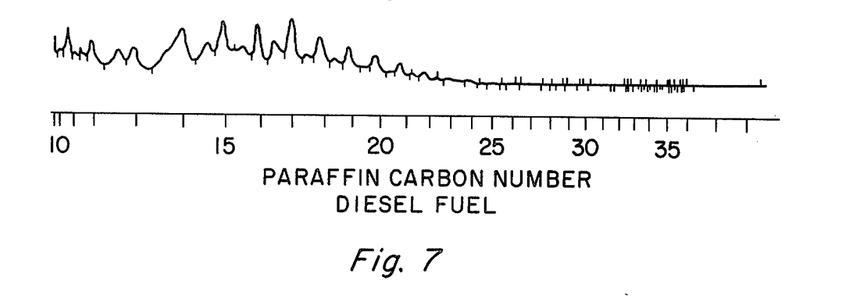
FIG. 7 is a gas chromatographic analysis of diesel fuel.
Figure 8:
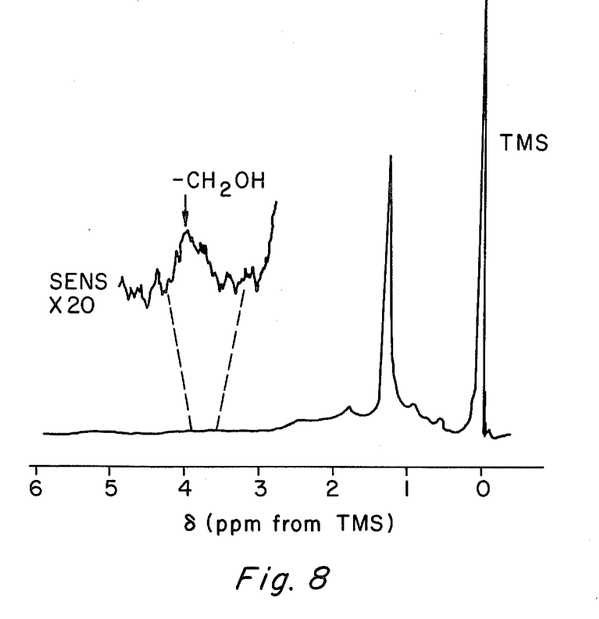
FIG. 8 is an nmr spectra for the product obtained with the process of the present invention.
Figure 9:
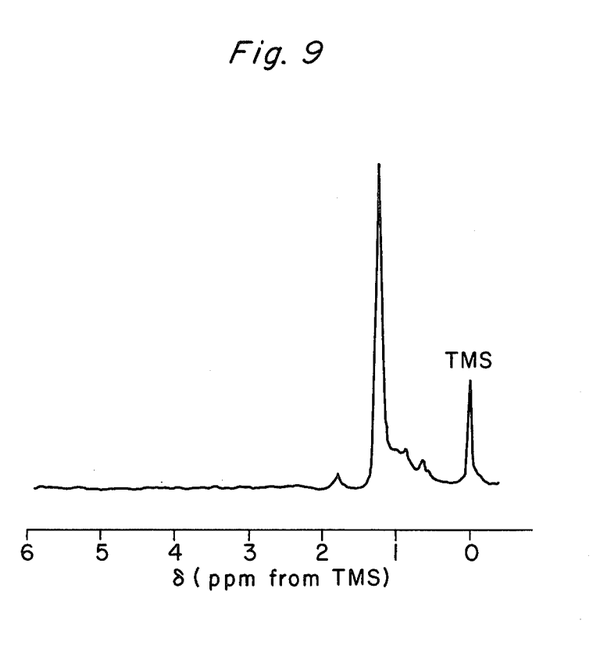
FIG. 9 is an nmr spectra for cetane.

Of particular importance is the fact that despite the wide range of pressures and temperatures which can be used as well as the diluteness of the gaseous feed streams, the product obtained is composed of highly desirable fractions of hydrocarbons. Typically, for example, the product obtained would have an analysis as shown by gas phase chromatography exemplified in FIG. 6. The distribution for diesel fuel is shown in FIG. 7. In particular, analysis of typical reaction products indicates a broad distribution of $C_1$ to $C_{40}$ paraffins. Only small amounts of $C_1$–$C_5$ alcohols have been detected with the catalyst of the invention. For example, a reaction employing 3 g of the present catalyst in 100 ml of xylene carried out under three separate synthesis gas chargings yielded a light yellow solution and water. The xylene was distilled under vacuum, a yellow oil resulted. Infrared analysis of the reaction solution and oil indicated only a small amount of oxygenated product and olefins and no metal carbonyl. Integrated nuclear magnetic resonance spectra of the yellow oil, shown in FIG. 8, indicated highly linear paraffinic products of an average chain length of 18 with little or no aromatics, unsaturates, oxygenates or branched products. Gas phase analysis of the gaseous components from the cooled reactor, as determined by gas-solid chromatography employing a thermal conductivity detector, indicated methane (generally less than 10 weight percent of hydrocarbon in the product), ethane, propane, butane, and only small amounts of unsaturated hydrocarbons.

An additional experiment was carried out to determine the efficacy of the catalyst in accordance with the present invention in dilute synthesis gas feed conditions. In particular, a catalyst was prepared from 3.4 grams of dicobalt octacarbonyl and 1.0 grams 5% palladium on alumina in cyclohexane under 400 psi of nitrogen and 1200 psi of hydrogen. The reactor was heated to about 180° C. However, no pressure drop was observed. On cooling the reactor, ammonia could not be detected in either the gas or liquid phases. Upon venting the gases and recharging with 500 psi of nitrogen and 500 psi of synthesis gas (2 $H_2$:1 CO) and thereafter heating, the catalyst exhibited normal activity for hydrocarbon synthesis. This is to be contrasted with ordinary Fischer-Tropsch catalysts which show a marked decrease in activity in the presence of a diluent.

That the catalyst of the present invention is substantially more reactive than conventionally known Fischer-Tropsch catalysts is shown in Table 1.

TABLE 1
REPRESENTATIVE HYDROCARBON PRODUCTION RATES OF FISCHER TROPSCH CATALYSTS

| Catalyst | Temperature °C. | Activity g prod. per Kg metal per hour |
|---|---|---|
| Catalyst of Example 4 | 225° | 3000 |
| Catalyst of Example 9 | 225° | 1080 |
| Catalyst of the Present Invention[a] | 125° | 40 |
| Lurgi catalyst (10Fe:10Cu: 2$K_2CO_3$:9$Al_2O_3$:30$SiO_2$)[b] | 225° | 24 |
| Brabag catalyst (100Fe:20Cu: 20Zn:1$K_2CO_3$)[b] | 225° | 10 |
| Bureau of Mines 2A catalyst (100Co:18Th$O_2$:100 kieselguhr)[c] | 195° | 50 |
| Pichler acid-promoted Ru/$Al_2O_3$ catalyst for polymethylene[d] | 120° | 120 |
| Kolbel slurry catalyst (100Fe:0.1Cu:0.05$K_2$O)[e] | 268° | 450 |

TABLE 1-continued
REPRESENTATIVE HYDROCARBON PRODUCTION RATES OF FISCHER TROPSCH CATALYSTS

| Catalyst | Temperature °C. | Activity g prod. per Kg metal per hour |
|---|---|---|
| Vannice (5% Fe on glassy carbon)[f] | 235° | 4 |

[a]2.2 g catalyst, containing 1.2 g metal on low surface area (80–100 mesh) $Al_2O_3$, 100 mL cyclohexane, 1200 psi charge 2.1 syngas, 300 mL AE reactor, catalyst prepared in situ.
[b]H. H. Storch, N. Golumbic, and R. B. Anderson, The Fischer-Tropsch and Related Syntheses, p. 308 (Table 86), Wiley, New York, 1951.
[c]Ibid., p. 132 (Table 5).
[d]H. Pichler and F. Bellstedt, Erdol u. Kohle 26, 560 (1973).
[e]H. Kolbel, P. Ackermann, and F. Engelhardt, Erdol u. Kohle 9, 153, 225, 303 (1956).
[f]M. A. Vannice, paper presented at 181st Am. Chem. Soc. Meet., Atlanta, GA, March 29-April 3, 1981.

Table 1 shows rate comparisons of a number of conventional Fischer-Tropsch catalysts with catalysts of the present invention under isothermal conditions. The activity of the present catalysts as expressed in conversions per catalytic volume per unit time or of conversions per mole of metal atoms per unit time are superior by about two orders of magnitude as compared to those catalysts studied by the Bureau of Mines.

Of particular interest is the fact that the conventional catalysts for hydrocarbon synthesis are generally used at about atmospheric pressure. In contrast, the catalysts of the present invention have their best activity at pressures between about 300 to 500 psi. An experiment utilizing a conventional Fischer-Tropsch catalyst, such as, 100 Co : 18 Th$O_2$ : 100 kieselguhr, under comparable conditions to those used with the present catalyst (cyclohexane slurry, 225° C., 1200 psi cold synthesis gas pressure), show that the rate of gas consumption was more than 10 times faster with the present catalyst, while the product of the present catalyst contained less of the undesired oxygenates.

Table 2 shows a comparison of several other types of catalysts with that of the present invention under the slurry conditions preferably employed when using the catalysts of the present invention.

TABLE 2
COMPARISON OF SEVERAL CATALYST SYSTEMS IN CYCLOHEXANE SLURRY[a]

| Catalyst | Activity g prod/(kg metal*hr) | Rate of Syngas Consumption | Gaseous Products, mmol | Consumption Ratio | Products |
|---|---|---|---|---|---|
| Catalyst of Example 4 | 3000 | 55%/20 min | 8.3 $CH_4$ 0.09 $C_2H_4$, 1.4 $C_3H_6$ 0.1 $C_4H_{10}$ 3.1 $CO_2$ | 2.2 2.0[b] | principally linear paraffins |
| Catalyst of the Present Invention prepared from 1 g 5% Pd on 80-100 mesh $Al_2O_3$ and 3.4 g $Co_2(CO)_8$, in situ (1.4 g catalyst containing 1.2 g metal) | 860 | 50%/70 min | 17 $CH_4$, 2.0 $C_2H_6$, 1.0 $CO_2$ | 2.0 1.9[b] | principally linear paraffins |
| Catalyst of Example 9 | 1080 | 33%/80 min | 13 $CH_4$, 1.4 $C_2H_6$ 0.5 $CO_2$ | 3.2 | principally hydrocarbons with small amounts of alcohols |
| Catalyst of Example 5 | 640 | 44%/60 min | 16 $CH_4$, 0.1 $C_2H_4$ 0.3 $C_2H_6$, 16 $CO_2$ | 1.7 | principally linear paraffins |
| Co on $Al_2O_3$, prepared from 1 g 80-100 mesh $Al_2O_3$ and 3.4 g $Co_2(CO)_8$ (2.2 g catalyst containing 1.2 g metal) | 270 | 33%/120 min | 18 $CH_4$, 0.9 $C_2H_6$, 2.3 $CO_2$ | 3.2 | hydrocarbons and alcohols |
| 5% Pd on 80-100 mesh $Al_2O_3$ (1 g of catalyst containing 0.05 g metal) | 0 | None | — | — | no hydrocarbons or alcohols detected |
| 100Co:18Th$O_2$:100 Kieselguhr (7.5 g of $K_2CO_3$ precipitated | 71 | 66%/350 min | 3.4 $CH_4$, 0.2 $C_2H_6$, 0.5 $CO_2$ | 2.3 | hydrocarbons, rich in lower molecular weight |

TABLE 2-continued

COMPARISON OF SEVERAL CATALYST SYSTEMS IN CYCLOHEXANE SLURRY[a]

| Catalyst | Activity g prod/(kg metal*hr) | Rate of Syngas Consumption | Gaseous Products, mmol | Consumption Ratio | Products |
|---|---|---|---|---|---|
| catalyst, reduced at 400° with $H_2$, containing 1.3 g Co) | | | | | oxygenates |
| 4Fe:1Cu (3 g of precipitated catalyst, reduced at 400° C. with $H_2$, containing 1.3 g Fe) | 180 | 40%/120 min | 2.4 $CH_4$, 24 $CO_2$ 1.2 $C_2H_4$, 0.8 $C_2H_6$ | 1.8 | hydrocarbons rich in olefins |
| 5% $Ru/Al_2O_3$ (2.2 g catalyst, containing 0.11 g metal) | 21000 | 48%/25 min | 27 $CH_4$, 0.02 $C_2H_4$ 0.13 $C_2H_6$ 0.14 $C_3H_8$, 1.6 $CO_2$ | 2.1 | principally linear paraffins, rich in high molecular weight waxes[c] |

[a]General Conditions: 100 mL cyclohexane, 300 mL AE reactor charged with 800 psi $H_2$ and 400 psi CO with reaction carried out at 225° C. (18 min to temperature).
[b]Consumption ratio, exclusive of methane formation.
[c]Significant quantities of soluble hydrocarbonyl and alklycarbonyl ruthenium complexes detected in solution by infrared.

While it is possible to prepare the present catalyst in the manner noted above and isolate the catalyst for storage and subsequent use, it is also possible to utilize the catalyst after it has been prepared in situ. In such a case, the catalyst would be prepared in the manner described hereinabove and one would simply continue to maintain the temperature and pressure conditions along with the appropriate amount of agitation to produce reaction of the gaseous materials and synthesis thereof into the desired hydrocarbons. The reaction is normally followed by continuous measurement of the pressure. When the pressure ceases to decrease, i.e., remains constant or decreases only slowly, it is apparent that the reaction is ceasing. Upon cooling, the hydrocarbons obtained are normally liquid and, in particular, dissolve in the solvent used. These can be isolated in the normal manner.

The catalysts of the present invention, their method of preparation and use are shown in the following examples:

EXAMPLE 1

The reactor configuration employed in most experiments is as follows. The reactor system consists of a 300 ml Autoclave Engineers Magne-Drive reactor, equipped with liquid and gas sampling valves. The heater is controlled by a Love Controls proportioning temperature controller, employing an iron-constantan thermocouple. Fine control of the temperature is achieved by means of alternating heating and cooling cycles in the vicinity of the set point. Cooling is controlled by the flow of compressed air through a solenoid-actuated internal, spiral cooling coil. Temperature may be readily controlled to within 2° C. Ordinarily, 100 mL of slurry solvent is employed, allowing for 200 mL of gas space. The system is normally purged with synthesis gas before final charging.

The above reactor was purged, 1 g of commercially obtained 5% palladium on alumina was added, followed by 3.4 g of commercially obtained octacarbonyldicobalt. While purging is continued, 100 mL of cyclohexane is added. The reactor is then sealed, purged with 500 psi synthesis gas, and after venting, charged with 1200 psi synthesis gas (nominally 2 $H_2$ : 1 CO). The reactor is checked for leaks. Stirring and heating are commenced with the temperature controller.

Approximately 18 minutes are required to bring the reactor to set temperature. As the temperature is increased, the pressure increases due to thermal expansion of the gases; however, in the range of 200°–225° C., the pressure levels off, then decreases, indicating that hydrocarbon synthesis has commenced. The reaction was carried out for a total elapsed time of 40 minutes, during which the pressure dropped from 2200 to 1590 psi at 225° C., affording an average pressure drop of 28 psi/min which corresponds to an average activity of 1200 g prod-(Kg metal)$^{-1}$ hr$^{-1}$ neglecting the formation of volatiles. The reactor was cooled to room temperature, at which the pressure was found to be 790 psi. Thus, taking into account those volatile materials which substantially condense at ambient pressure, the gross activity is 1300 g prod-(Kg metal)$^{-1}$ hr$^{-1}$. Theoretically, 2.2 g of the catalyst was formed.

EXAMPLE 2

The reaction mixture from Example 1 was allowed to stand overnight. The gases were vented, the solvent was drawn off, and the catalyst washed with cyclohexane. While purging with argon, 100 ml fresh cyclohexane was added. During the solvent removal and washing, approximately 0.3 g of the catalyst was lost. The reactor was again recharged with 1200 psi synthesis gas and brought to 225° C. During the 50 minutes of use the pressure dropped from 2080 to 1520 psi, affording an activity of 840 g prod-(Kg metal)$^{-1}$ hr$^{-1}$. Upon cooling, the pressure was found to be 610 psi. Thus, using the pressure drop at room temperature, the activity is found to be 1490 g prod-(Kg metal)$^{-1}$ hr$^{-1}$.

The cooled reaction mixture was subjected to gas analysis. This is accomplished by injecting 0.500 ml of reaction gas into a gas chromatograph equipped with dual thermistor-type thermal conductivity detectors. Gas analysis for hydrogen is achieved with a 6 foot × ¼ inch glass column, packed with Linde 13× molecular sieve, and employing nitrogen as carrier gas at ambient temperatures. Gas analysis for carbon monoxide and methane is achieved with a 1 meter × ¼ inch polyethylene column, also packed with Linde 13× molecular sieve and employing helium as carrier gas at ambient temperature. Gas analysis for carbon dioxide, ethylene and ethane is achieved with a 4½ foot × ¼ inch polyethylene column packed with Chromosorb 102 and also employing helium as carrier gas at ambient temperature. Gas analysis for higher volatile hydrocarbons is achieved on a gas chromatograph equipped with hot wire-type thermal conductivity detectors by means of a gas sampling value, and using a 12 foot × ⅛ inch Porapak Q stainless steel column at 150° C., employing helium as carrier gas.

The areas of the respective peaks are integrated digitally and compared to the areas of corresponding injections of the pure components. For the instant example, the gas phase was found to consist of 59% $H_2$, 35% CO, 5% $CH_4$, 0.5% $CO_2$, 0.4% $C_2H_6$ and 0.03% $C_2H_4$. The ideal gas law is then employed to estimate the quantity of each gas present in the gas phase. In this particular case, the gas phase consisted of 202 mmol $H_2$, 119 mmol CO, 18 mmol $CH_4$, 1.6 mmol $CO_2$, 1.5 mmol $C_2H_6$ and 0.1 mmol $C_2H_4$. The consumption ratio is then 2.3, with 247 mmol $H_2$ and 106 mmol CO having been consumed. The methane fraction corresponds to approximately 4.5% by weight of the hydrocarbon product.

The bulk of the solution, containing dissolved hydrocarbons is transferred to a bottle by means of the liquid sampling valve. The remainder of the solution is removed by pipette after the reactor is vented and opened. Ordinarily, copious amounts of water are present at the bottom of the reactor, near the catalyst. The catalyst is then removed from the reactor by use of a magnet and transferred to a petri dish, in which it is dried in an oven at 100°–120° C.; 1.86 g of catalyst was so recovered.

EXAMPLE 3

1.35 g of the catalyst recovered in Example 2 was packed into a stainless steel tube of ¼" nominal diameter. The catalyst was retained by glass wool plugs at each end of the bed. Synthesis gas (66% $H_2$, 34% CO) at 5 psi was passed through the catalyst bed, affording a flow rate of 0.16 ft³/hr. The gas passed through the column was analyzed periodically by gas chromatography (He carrier gas) by means of a metering gas sampling valve.

The temperature was gradually increased, and at 125° C., only a small portion (0.04%) was found to have been consumed. At 150° C., approximately 1% of the carbon monoxide was converted to products. Increasing the temperature to 225° C. led to very high conversions (initially about 80% after 5 min and 98% after 15 min). However, the activity gradually dropped (78% after 1 hour, 72% after 2 hours, 49% after 3 hours, 54% after 4 hours, and 37% CO conversion after 6 hours). Flushing hydrogen over the catalyst at 225° C. failed to restore the high activity, although a modest improvement in activity was observed. At the end of the reaction the material in the cold trap was found to weigh 1.7 g and consisted almost exclusively of water; that is the products were predominately low-boiling.

EXAMPLE 4

The 0.3L autoclave was purged with argon. One gram of commercially obtained 5% platinum on alumina hydrogenation catalyst was added, followed by 100 ml cyclohexane. After further purging, 3.4 g of commercially obtained octacarbonyldicobalt was added. The reactor was then sealed, purged two times with 200 psi syngas and then charged with 1200 psi of syngas, consisting of two parts hydrogen to one part carbon monoxide. The reactor was checked for leaks. Approximately 18 minutes were required to achieve an operating temperature of 225° C. During the warm-up cycle, the pressure increased to 2075, after which time the pressure decreased at an average rate of 39.5 psi/min (see Table E-4 which follows).

TABLE E-4

| RATE OF SYNGAS CONSUMPTION | | |
|---|---|---|
| Time, min | Temp, °C. | Pressure, psi |
| 0 | 25 | 1200 |
| 15 | 200 | 1950 |
| 18 | 225 | 2075 |
| 20 | 225 | 2000 |
| 22 | 230 | 1825 |
| 25 | 225 | 1625 |
| 28 | 225 | 1500 |

TABLE E-4-continued

| RATE OF SYNGAS CONSUMPTION | | |
|---|---|---|
| Time, min | Temp, °C. | Pressure, psi |
| 30 | 225 | 1425 |
| 32 | 225 | 1375 |
| 35 | 225 | 1300 |
| 40 | 225 | 1210 |

The reactor was cooled to room temperature, at which the pressure was found to be 540 psi. The gas phase was analyzed and contained 39.9% hydrogen, 50.1% carbon monoxide, 8.3% methane, 0.03% ethylene, 0.45% ethane, 0.34% propane, and 1.0% carbon dioxide. The consumption ratio was found to be 2.2; when corrected for the methane produced, the consumption ratio was calculated to be 2.0.

Upon opening the reactor, the liquid phase was clear and slightly yellow. A small amount of black liquid consisting of water and suspended catalyst, was found at the bottom of the reactor. The catalyst was removed magnetically and dried overnight at 120° C. The sample of recovered catalyst weighed 1.5 g. Gas chromatography analysis of the liquid phase indicates predominately linear aliphatic hydrocarbons are formed.

EXAMPLE 5

A sample of 7.2 g commercial zinc oxide was suspended in 15 ml distilled water. A solution of 0.5 g palladium (I) chloride, 8 ml concentrated hydrochloric acid and 10 ml water was added. The slurry was heated to dryness with constant stirring by means of a glass rod, yielding a red-brown solid. This solid was dried for 20 hrs at 120° C. in an oven. Reduction in a stream of hydrogen at 220°–240° C. for 3 hrs afforded 7.55 g of 4% palladium on zinc oxide.

One gram of said 4% Pd/ZnO was added to the 0.3L reactor purged with argon and containing 100 mL cyclohexane as slurry solvent. 3.4 g of octacarbonyldicobalt, containing considerable amounts of the purple contaminant familiar to those acquainted with this reagent was added. The reactor was purged two times with 200 psi syngas, then pressurized to 1200 psi with syngas consisting of 67% $H_2$ and 33% CO.

The reactor was warmed to 225° C., at which time a liquid sample indicated little soluble cobalt species. Over an hour period little activity for syngas consumption was observed. The reactor was cooled to 80° C. and maintained at this temperature for 3 hours. A liquid sample indicated the presence of $Co_2(CO)_8$. The reactor was cooled to room temperature.

On the following day, the reactor was heated again to 225° C. During the following hour, the pressure decreased at a rate of 8 psi/min. Upon cooling the pressure was 560 psi. Gas analysis indicated the following mmol quantities of gaseous products:

16 $CH_4$, 0.1 $C_2H_4$, 0.3 $C_2H_6$, and 16 $CO_2$. The consumption ratio was 1.7.

The solution removed from the reactor was slightly yellow. Washing the reactor and catalyst with tetrahydrofuran led to a blue solution. Addition of water to this blue solution led to a pale pink color, suggesting that some cobalt was not tightly bound to the heterogeneous catalyst. The catalyst was washed with tetrahydrofuran until the washings were colorless. 1.9 g of catalyst was recovered magnetically; approximately 0.2 g of material was non-magnetic, and this is ascribed to impurities in the octacarbonyldicobalt starting material.

EXAMPLE 6

A 250 ml three neck round bottom flask was purged with argon. One gram of 5% $Pd/Al_2O_3$ and a magnetic stirring bar was added. With continued purging, 100 ml of decalin was added, followed by 3.4 g $Co_2(CO)_8$. The argon was replaced with a slow, steady flow of hydrogen. The reaction mixture was heated with stirring and was maintained at 135° C.–140° C. After 3 hours, the infrared spectrum of the reaction solution indicated the absence of any metal carbonyl species. On cooling, it was found that a magnetic catalyst, clinging to the magnetic stirring bar, was formed. Upon filtration and drying this catalyst displayed comparable activities for hydrocarbon synthesis as those prepared by the method of Example 1.

EXAMPLE 7

The 0.3L autoclave was purged with argon. Two grams of 5% $Pd/Al_2O_3$ was added, followed by 150 ml cyclohexane, then 6.8 g cobalt carbonyl. The reactor was charged with 870 psi $H_2$ and 430 psi CO. The reactor was heated to 225° C., after which the pressure was found to decrease at an average rate of 54 psi/min. Gas chromatographic analysis indicated the following gas composition: 65.6% $H_2$, 27.6% CO, 4.4% $CH_4$, 1.1% $CO_2$ and 0.17% $C_2H_6$.

EXAMPLE 8

In this reaction, a 310 ml packed cone autoclave, manufactured by Parr Instruments was employed. The reactor was purged with argon. 3.42 g $Co_2(CO)_8$, 1.06 g 5% $Pd/Al_2O_3$ and 100 ml tetrahydrofuran were added. The reactor was charged with 1300 psi synthesis gas, consisting of hydrogen and carbon monoxide in equal proportions. The reactor was heated to 200° C. The pressure dropped from 1600 to 1100 psi over 3.5 hrs. Upon cooling, the pressure was 350 psi. Very little hydrogen was found in the gas phase. A significant quantity of white, waxy, tetrahydrofuran-insoluble material was observed.

Infrared spectra and toluene solubility indicate this to be higher molecular weight paraffins.

EXAMPLE 9

Chromatographic alumina was sieved to be 80 to 100 mesh. Five grams of this alumina was suspended in 5 g water. A solution of 0.44 g $PdCl_2$, 7 ml hydrochloric acid and 10 ml $H_2O$ was added. The slurry was heated with stirring to dryness on a hot plate, then dried at 120° C. for 16 hrs.

The resulting solid was carefully ground to achieve approximately the same dimensions as the starting support. It was then reduced for 2 hrs at 220°–250° C. under a stream of $H_2$.

One gram of the said 5% palladium dispersed on alumina was added to the 0.3L autoclave. The reactor was purged with argon and 100 ml cyclohexane was added. 1.13 g cobalt carbonyl was then added. The reactor was purged with syngas, then pressurized to 1200 psi ($2H_2$:1CO). The reactor was heated to 225° C. During the following 80 minutes, the pressure dropped 510 psi.

Upon cooling, the final pressure was 800 psi. The gas phase consisted of 55% $H_2$, 42% CO, 2.8% $CH_4$, 0.3% $C_2H_6$ and 0.1% $CO_2$.

We claim:

1. A method for synthesizing principally normally liquid liner paraffinic hydrocarbons in an organic solvent comprising contacting a mixture of hydrogen and carbon monoxide with a slurry of a catalyst prepared by the process of immersing a heterogeneous component, composed of palladium or platinum or mixtures thereof deposited on a solid phase, into a solution of cobalt carbonyl or cobalt carbonyl precursors which on heating form the cobalt carbonyl, and heating the resulting mixture at a temperature from about 100° to 350° C. under pressure.

2. The method of claim 1, wherein the amount of palladium or platinum in the catalyst system is in the range from about 0.1 to 10 weight percent based on the total weight of the catalyst.

3. The method of claim 1, wherein the amount of cobalt in the catalyst system is in the range of from about 10 to 70 weight percent based on the total weight of the catalyst.

4. The method of claim 1, wherein the solid phase is selected from the group consisting of alumina, silica gel, kieselguhr and zinc oxide.

5. The method of claim 1, wherein the slurry concentration is in the range from about 0.3 to 50 percent by volume.

6. The method of claim 1, wherein the reaction to synthesize said linear paraffinic hydrocarbons is carried out at a temperature from about 100° to 300° C.

7. The method of claim 6, wherein the temperature is from about 130° to 250° C.

* * * * *